United States Patent
Niwa

(10) Patent No.: US 8,384,729 B2
(45) Date of Patent: Feb. 26, 2013

(54) MEDICAL IMAGE DISPLAY SYSTEM, MEDICAL IMAGE DISPLAY METHOD, AND MEDICAL IMAGE DISPLAY PROGRAM

(75) Inventor: Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 786 days.

(21) Appl. No.: 11/554,831

(22) Filed: Oct. 31, 2006

(65) Prior Publication Data
US 2007/0109402 A1 May 17, 2007

(30) Foreign Application Priority Data

Nov. 1, 2005 (JP) .................................. 2005-318716

(51) Int. Cl.
*G09G 5/00* (2006.01)
(52) U.S. Cl. ........ 345/581; 345/619; 345/660; 715/243; 715/244; 715/245; 715/246; 715/253
(58) Field of Classification Search ...... 430/7; 600/410; 705/2
See application file for complete search history.

(56) References Cited

U.S. PATENT DOCUMENTS

| | | | | |
|---|---|---|---|---|
| 5,734,915 | A * | 3/1998 | Roewer ........................ | 715/202 |
| 6,912,061 | B1 * | 6/2005 | Ozaki .......................... | 358/1.15 |
| 2003/0174872 | A1 | 9/2003 | Chalana et al. ............... | 382/128 |
| 2004/0068170 | A1 * | 4/2004 | Wang et al. .................... | 600/407 |
| 2006/0058624 | A1 * | 3/2006 | Kimura ......................... | 600/407 |
| 2006/0079755 | A1 * | 4/2006 | Stazzone et al. ............. | 600/410 |
| 2006/0111935 | A1 * | 5/2006 | Bao et al. .......................... | 705/2 |
| 2006/0111937 | A1 * | 5/2006 | Yarger et al. ...................... | 705/2 |
| 2006/0177114 | A1 * | 8/2006 | Tongdee et al. ............... | 382/128 |
| 2006/0241408 | A1 * | 10/2006 | Yakubovsky et al. ......... | 600/429 |
| 2006/0242143 | A1 * | 10/2006 | Esham et al. ...................... | 707/6 |
| 2006/0251975 | A1 * | 11/2006 | Taranath et al. .................. | 430/7 |

FOREIGN PATENT DOCUMENTS

| | | |
|---|---|---|
| JP | 64-013676 | 1/1989 |
| JP | 04-049945 | 2/1992 |
| JP | 4-49945 | 2/1992 |

(Continued)

OTHER PUBLICATIONS

Japanese Office Action issued Apr. 17, 2012 in patent application No. 2006-297552.
Japanese Office Action mailed Dec. 11, 2012 issued in Japanese Patent Application No. 2006-297552.

*Primary Examiner* — Xiao M. Wu
*Assistant Examiner* — Phi Hoang
(74) *Attorney, Agent, or Firm* — Oblon, Spivak, McClelland, Maier & Neustadt, L.L.P.

(57) ABSTRACT

A multi-modality medical image display system, having a storage device that stores image attributes indicating attributes of an image, and information indicating a plurality of display layouts, each combination set in accordance with at least one of a first or second modality type, and corresponding to one of the plurality of display layouts. The system further includes a unit configured to select a combination of image attributes for the requested medical image information based on incidental information that is assigned to the requested medical image information. The system further includes a unit configured to compare the combination of image attributes of the requested medical image information with the combination of the image attributes and, based on the comparison, and to search the storage device and obtain therefrom one of the plurality of display layouts that corresponds with the combination of image attributes of the requested medical image information.

28 Claims, 11 Drawing Sheets

| IMAGE ATTRIBUTE/ COMBINATION OF IMAGE ATTRIBUTES | IMAGE ATTRIBUTE | MEDICAL IMAGE | INFORMATION ON DISPLAY FRAME | | |
|---|---|---|---|---|---|
| | | | DISPLAY/ NON-DISPLAY | WHERE / POSITION ON DISPLAY FRAME | HOW / CONTENT OF DISPLAY FRAME |
| CT APPARATUS | CT APPARATUS | CT IMAGE | DISPLAY | (1, 1) | STACK DISPLAY |
| MR APPARATUS | MR APPARATUS | MR IMAGE | DISPLAY | (1, 1) | TILE DISPLAY |
| CR APPARATUS | CR APPARATUS | CR IMAGE | DISPLAY | (1, 1) | STACK DISPLAY |
| CT APPARATUS+ MR APPARATUS | CT APPARATUS | CT IMAGE | DISPLAY | TWO PARTS IN HORIZONTAL DIRECTION (1, 1) | STACK DISPLAY |
| | MR APPARATUS | MR IMAGE | DISPLAY | TWO PARTS IN HORIZONTAL DIRECTION (2, 1) | TILE DISPLAY |
| CT APPARATUS+ CR APPARATUS | CT APPARATUS | CT IMAGE | DISPLAY | TWO PARTS IN HORIZONTAL DIRECTION (1, 1) | STACK DISPLAY |
| | CR APPARATUS | CR IMAGE | DISPLAY | TWO PARTS IN HORIZONTAL DIRECTION (2, 1) | STACK DISPLAY |
| CT APPARATUS+ MR APPARATUS+ CR APPARATUS | CT APPARATUS | CT IMAGE | DISPLAY | FOUR PARTS IN VERTICAL DIRECTION AND IN HORIZONTAL DIRECTION (1, 1) | STACK DISPLAY |
| | MR APPARATUS | MR IMAGE | DISPLAY | FOUR PARTS IN VERTICAL DIRECTION AND IN HORIZONTAL DIRECTION (1, 2) | TILE DISPLAY |
| | CR APPARATUS | CR IMAGE | DISPLAY | FOUR PARTS IN VERTICAL DIRECTION AND IN HORIZONTAL DIRECTION (2, 1) - (2, 2) | STACK DISPLAY |
| CT APPARATUS+ MR APPARATUS+ CR APPARATUS | CT APPARATUS | CT IMAGE | DISPLAY | FOUR PARTS IN VERTICAL DIRECTION AND IN HORIZONTAL DIRECTION (1, 1) - (2, 1) | STACK DISPLAY |
| | MR APPARATUS | MR IMAGE | DISPLAY | FOUR PARTS IN VERTICAL DIRECTION AND IN HORIZONTAL DIRECTION (1, 2) - (2, 2) | TILE DISPLAY |
| | CR APPARATUS | CR IMAGE | NON-DISPLAY | — | — |
| ⋮ | ⋮ | ⋮ | ⋮ | ⋮ | ⋮ |

FOREIGN PATENT DOCUMENTS

| | | |
|---|---|---|
| JP | 2005-149107 A | 6/2005 |
| JP | 2005-245921 | 9/2005 |
| JP | 2005-305562 | 11/2005 |

* cited by examiner

BLANK AREA

INCIDENTAL INFORMATION AREA

| (0008, 1010) | STATION NAME |
| (0008, 0060) | MODALITY |
| (0008, 0020) | EXAMINATION DATE |
| (0010, 0010) | PATIENT NAME |
| (0028, 1050) | CENTER OF WINDOW PROPER TO IMAGE |
| (0028, 1051) | WINDOW WIDTH PROPER TO IMAGE |

(0000, qqqq)

IMAGE DATA AREA

| IMAGE ATTRIBUTE/ COMBINATION OF IMAGE ATTRIBUTES | IMAGE ATTRIBUTE | MEDICAL IMAGE | INFORMATION ON DISPLAY FRAME ||| 
|---|---|---|---|---|---|
| | | | DISPLAY/ NON-DISPLAY | WHERE / POSITION ON DISPLAY FRAME | HOW / CONTENT OF DISPLAY FRAME |
| CT APPARATUS | CT APPARATUS | CT IMAGE | DISPLAY | (1, 1) | STACK DISPLAY |
| MR APPARATUS | MR APPARATUS | MR IMAGE | DISPLAY | (1, 1) | TILE DISPLAY |
| CR APPARATUS | CR APPARATUS | CR IMAGE | DISPLAY | (1, 1) | STACK DISPLAY |
| CT APPARATUS+ MR APPARATUS | CT APPARATUS | CT IMAGE | DISPLAY | TWO PARTS IN HORIZONTAL DIRECTION (1, 1) | STACK DISPLAY |
| | MR APPARATUS | MR IMAGE | DISPLAY | TWO PARTS IN HORIZONTAL DIRECTION (2, 1) | TILE DISPLAY |
| CT APPARATUS+ CR APPARATUS | CT APPARATUS | CT IMAGE | DISPLAY | TWO PARTS IN HORIZONTAL DIRECTION (1, 1) | STACK DISPLAY |
| | CR APPARATUS | CR IMAGE | DISPLAY | TWO PARTS IN HORIZONTAL DIRECTION (2, 1) | STACK DISPLAY |
| CT APPARATUS+ MR APPARATUS+ CR APPARATUS | CT APPARATUS | CT IMAGE | DISPLAY | FOUR PARTS IN VERTICAL DIRECTION AND IN HORIZONTAL DIRECTION (1, 1) | STACK DISPLAY |
| | MR APPARATUS | MR IMAGE | DISPLAY | FOUR PARTS IN VERTICAL DIRECTION AND IN HORIZONTAL DIRECTION (1, 2) | TILE DISPLAY |
| | CR APPARATUS | CR IMAGE | DISPLAY | FOUR PARTS IN VERTICAL DIRECTION (2, 1)- (2, 2) | STACK DISPLAY |
| CT APPARATUS+ MR APPARATUS+ CR APPARATUS | CT APPARATUS | CT IMAGE | DISPLAY | FOUR PARTS IN VERTICAL DIRECTION AND IN HORIZONTAL DIRECTION (1, 1)- (2, 1) | STACK DISPLAY |
| | MR APPARATUS | MR IMAGE | DISPLAY | FOUR PARTS IN VERTICAL DIRECTION AND IN HORIZONTAL DIRECTION (1, 2)- (2, 2) | TILE DISPLAY |
| | CR APPARATUS | CR IMAGE | NON-DISPLAY | — | — |
| ---- | ---- | ---- | ---- | ---- | ---- |

MEDICAL IMAGE DISPLAY SYSTEM, MEDICAL IMAGE DISPLAY METHOD, AND MEDICAL IMAGE DISPLAY PROGRAM

BACKGROUND OF THE INVENTION

1. Field of the Invention

The present invention relates to a medical image display system comprising a server or a network attached storage (NAS) that stores a medical image (image information) and an image display terminal connected thereto via a network, a medical image display method, and a medical image display program.

2. Description of the Related Art

In image diagnosis, an image shot by a modality (medical-image tomography apparatus) such as a computed tomography (CT) apparatus, a computed radiography (CR) apparatus, a magnetic resonance (MR) apparatus, and a digital radiography (DR) apparatus is output to a film or is displayed on a client viewer, and a doctor interprets (diagnoses) the image.

Recently, an image data system such as a picture archiving and communication system (PACS) has been widespread. With the PACS, a server in a medical care facility in a hospital, etc. is connected to an image display terminal such as a workstation that is capable of displaying an image, thereby structuring a system that can communicate the medical image. The PACS includes a structure having the server, a plurality of NASs on the network and a client viewer that displays the medical image stored in the NASs for interpretation. A plurality of modalities (multi-modality) individually capture images of a patient in advance and obtain the medical images. The server stores the medical images of the patient with a correspondence to a display layout for displaying the medical images every modality that captures the image. An interpreter (doctor, etc.) selects the patient and the modality, and only the medical image of the patient captured with the modality is displayed on the client viewer on the PACS in a proper display configuration.

For example, only a plurality of CT images of the patient are displayed on the client viewer on the PACS on a preset display configuration. A user arbitrarily classifies the CT images into a series of the head, chest, and abdomen on a screen of the client viewer, and manually changes the display configuration.

Further, with the client viewer on the PACS, the development of technologies requires not only the display of only the medical image captured with a single modality but also the display and interpretation of all medical images (including images after image processing) of the patient on the client viewer, irrespective of the type of modality.

Further, it is required, to a multi-modality client viewer that uses a plurality of modalities, that the medical images of the patient, generated with a plurality of modalities, are efficiently arranged and displayed on the same screen. However, according to a conventional technology, as a display configuration, a single modality is optimally displayed. Therefore, initially, the images are overlaid and displayed on the screen. As a consequence, the client viewer requires the display change for easy interpretation, and the diagnostic efficiency of the doctor is low.

SUMMARY OF THE INVENTION

The present invention has taken into consideration the above-described problems, and it is an object of the present invention to provide a medical image display system, a medical image display method and a medical image display program such that it supports an efficiency of comparison and interpretation of various medical images, executed on an image display terminal.

To solve the above-described problems, the present invention provides the medical image display system to mention it in claim 1, comprising: a storage device configured to store a combination of a plurality of image attributes and information on a display-format with a correspondence therebetween; an input device configured to make a request of a display of image information; a combination determining unit configured to determine a combination of image attributes about the request on the basis of incidental information added to the image information; an information on display-format searching unit configured to search and obtain information on a display-format corresponding to the combination of the image attributes about the request from the storage device by comparing the combination of the image attributes about the request with the combination of the image attributes stored in the storage device; a medical-image display information generating unit configured to generate medical-image display information by arranging the image information made the request in accordance with the information on the display-format obtained by the searching unit; and a display control unit configured to make display the medical-image display information.

To solve the above-described problems, the present invention provides the medical image display method to mention it in claim 27, comprising steps of: storing a combination of a plurality of image attributes and information on a display-format with a correspondence therebetween; making a request of a display of image information; determining a combination of image attributes about the request on the basis of incidental information added to the image information; searching and obtaining information on a display-format corresponding to the combination of the image attributes about the request by comparing the combination of the image attributes about the request with the combination of the image attributes stored by the step of storing; generating medical-image display information by arranging the image information made the request in accordance with the information on the display-format obtained by the searching and obtaining; and making display the medical-image display information.

To solve the above-described problems, the present invention provides the medical image display program to mention it in claim 28, enabling a computer, having a storage device that stores a combination of a plurality of image attributes and information on a display-format with a correspondence therebetween and an input device that makes a request of a display of image information, to execute processing, the medical image display program comprising steps of: determining a combination of image attributes about the request on the basis of incidental information added to the image information; searching and obtaining information on a display-format corresponding to the combination of the image attributes about the request from the storage device by comparing the combination of the image attributes about the request with the combination of the image attributes stored in the storage device; generating medical-image display information by arranging the image information made the request in accordance with the information on the display-format obtained by the function to search and obtain; and making display the medical-image display information.

Therefore, according to the present invention to provide the medical image display system, the medical image display method and the medical image display program, it is possible to support an efficiency of comparison and interpretation of various medical images, executed on an image display terminal.

BRIEF DESCRIPTION OF THE DRAWINGS

In the accompanying drawings:

FIG. 2 is a diagram showing one example of the DICOM file;

FIG. 7 is a diagram showing information on display-format DB as a table;

DESCRIPTION OF THE PREFERRED EMBODIMENTS

Hereinbelow, a detailed description is given of a medical image display system, a medical image display method, and a medical image display program according to preferable embodiments of the present invention with reference to the drawings.

Figure 1:
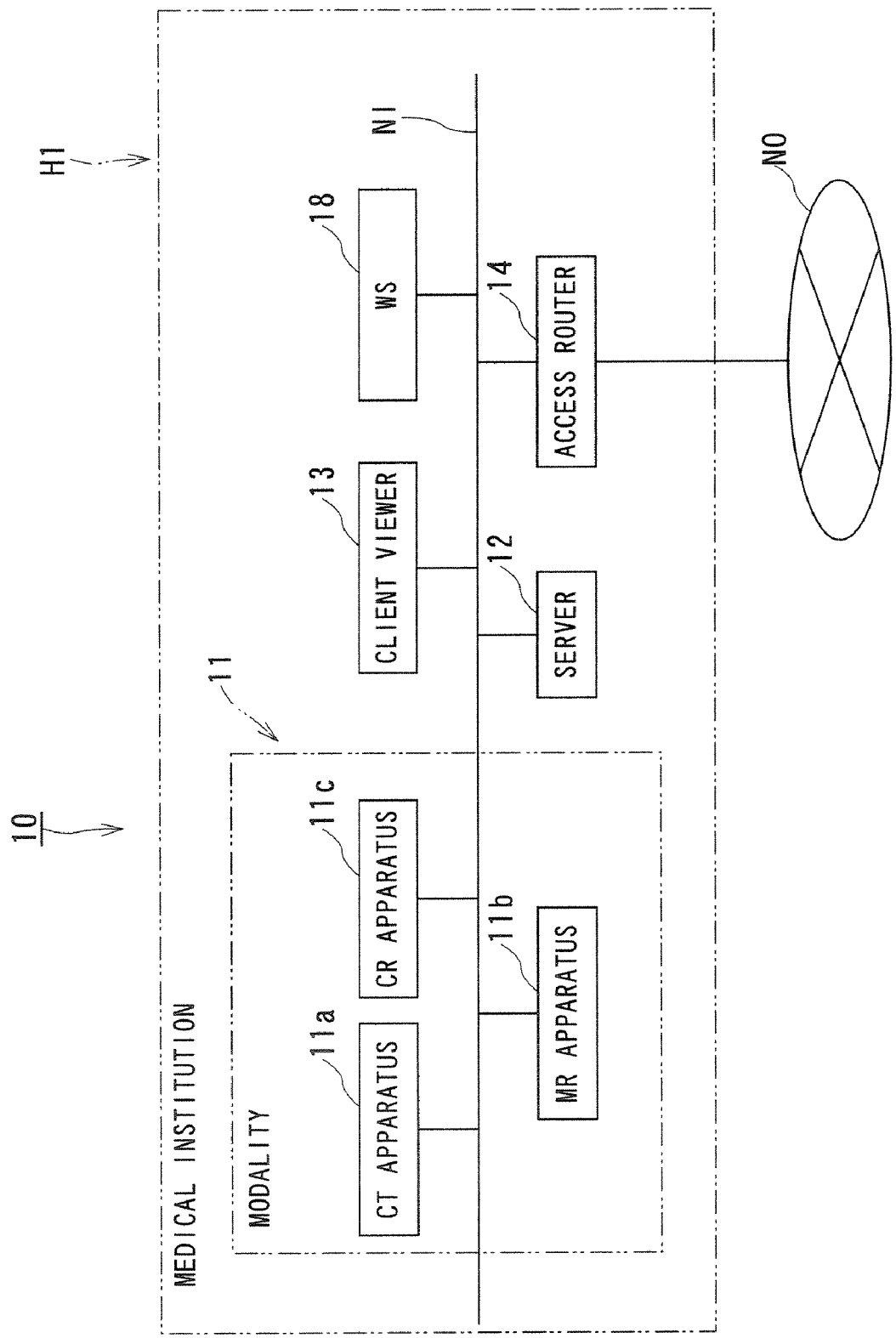
FIG. 1 is a schematic diagram showing the entire outline of the medical image display system according to the first embodiment of the present invention.
Figure 3:
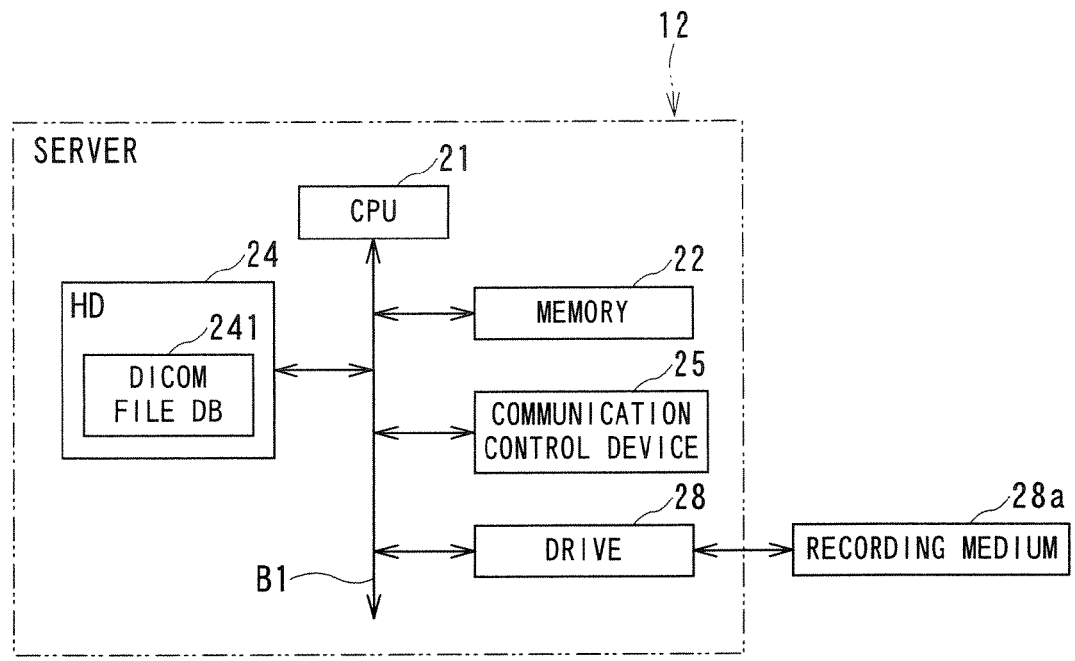
FIG. 3 is a block diagram showing a hardware structure of a server.
Figure 4:
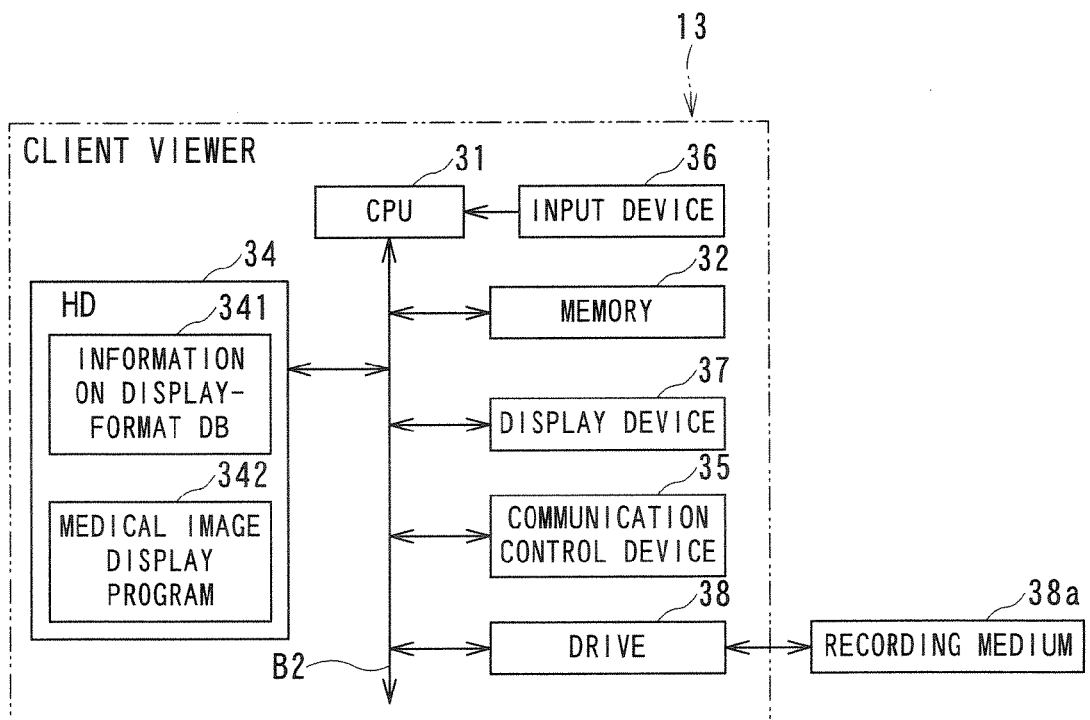
FIG. 4 is a block diagram showing a hardware structure of a client viewer.

FIGS. 1, 3, and 4 show a medical image display system according to the first embodiment of the present invention. FIG. 1 is a schematic diagram showing the entire outline of the medical image display system.

Referring to FIG. 1, a medical image display system 10 according to the present invention is shown. The medical image display system 10 stores in advance a combination of image attributes having a plurality of image attributes and information on a display-format for each combination of the image attributes with a correspondence therebetween. Further, upon displaying the medical image (image information) whose a display is required, the medical image display system 10 arranges a medical image required the display in the pre-stored information on the display-format, generates medical-image display information, and automatically displays the medical-image display information. Herein, the information on the display-format comprises information on a display frame every image attribute. The information on the display frame indicates "display" or "non-display" of the medical image corresponding to the image attribute and where (position on the display frame) or/and how (content of the display frame) the medical image is to be displayed on an image-plane, displayed on a screen, in the case of the "display". It is noted that the information on the display-format is set in advance every user and every terminal. Alternatively, the information on the display-format may be preset every system by cooperating a plurality of medical care facilities as one system.

Hereinbelow, as long as a description is not given, the image attribute will be described as the image attribute depending on a type of a modality (modality type). However, the present invention is not limited to this. The image attribute may be depending on, e.g., apparatus information, an image capturing time-internal, an image-captured portion, a medical image direction (axial, sagittal, or coronal), information on image processing of the medical image, or a type of a server. Alternatively, the image attribute may be an image attribute depending on a combination of the modality type.

The medical image display system 10 has a modality (medical-image tomography apparatus) 11 that generates a medical image such as bit map data by image capturing and generates a digital imaging and communication in medicine (DICOM) file as an example of a medical image file every medical image, a server 12 that obtains the DICOM file generated by the modality 11 and stores and manages the DICOM file, and a client viewer 13 as an image display terminal that loads the DICOM file from the server 12 and displays the medical image. The components in the medical image display system 10 are connected to each other via an in-organization network NI such as a local area network (LAN). The server 12 is connected to the client viewer 13 via the in-organization network NI, thereby structuring an image data management system such as a picture archiving and communication system (PACS). It is noted that one server 12 and one client viewer 13 are disposed in a medical institution H1 as shown in FIG. 1. Alternatively, a plurality of the servers 12 and the client viewers 13 may be disposed in the medical institution H1.

Further, on the network NI in the organization of the medical image display system 10, an access router 14 may be disposed as data relay system that relays data communication with another medical care facility (not shown) via a network NO out of the organization. The network NO out of the organization may be a line connection such as a public line (including an integrated services digital network (ISDN)) or a dedicated line. Alternatively, the network NO out of the organization may be an open network such as the Internet.

Further, on the network NI in the organization of the medical image display system 10, a workstation (WS) 18 may be disposed as an image processing terminal basically comprising a computer. The WS 18 performs image processing of the medical image, such as a shaded volume rendering (SVR) processing, a maximum intensity projection (MaxIP) processing, a minimum intensity projection (MinIP) processing, an X-ray intensity projection (IP) processing, and a multiple plane rendering (MPR) processing. The medical image after the image processing is stored and managed by the server 12.

The modality 11 is, e.g., a computed tomography (CT) apparatus 11a, a magnetic resonance (MR) apparatus 11b, or a computed radiography (CR) apparatus 11c. It is noted that the DICOM file is not necessarily generated by the modality 11. For example, the DICOM file may be generated by the server 12 on the basis of an original image received from the modality 11. Herein, the DICOM file is generated by the modality 11 in accordance with a DICOM standard. The DICOM standard is standardized in the US so as to make the medical information common.

FIG. 2 is a diagram showing one example of the DICOM file. Referring to FIG. 2, the DICOM file generated by the modality 11 every generated medical image mainly comprises a blank area, an incidental information area, and an image data area. The incidental information area of the DICOM file comprises a set of data elements, and each data element includes a standard tag (group number and element number) and tag information thereof (data length and data). The tag information indicates various attribute information on the image, including patient information, information on a shooting condition, image information, and display information.

The patient information includes personal information that specifies the patient, such as a patient name, a patient identification (ID), and a birth date. The information on the shooting condition includes information on the shooting situation, such as an image type having a primary obtained image and a secondary obtained image, an image captured portion, and an X-ray current value and a voltage value upon shooting with the modality 11. The image information includes information indicating an examination ID and the modality type. The display information includes information such as an image contrast, image arrangement order or arrangement, and a series NO. (group ID of the medical image). Other information includes a file code of the DICOM file.

For example, embedded to the incidental information area of the DICOM file about one piece of image data are a standard tag (0008, 1010) indicating the station name and tag information thereof, a standard tag (0008, 0060) indicating the modality and tag information thereof, a standard tag (0008, 0020) indicating the examination date and tag information thereof, a standard tag (0010, 0010) indicating the patient name and tag information thereof, a standard tag (0028, 1050) indicating the center of a window proper to the image and tag information thereof, a standard tag (0028, 1051) indicating a window width proper to the image and tag information thereof, and standard tag (oooo, qqqq) indicating the sequential data is image data. It is noted that the tag and data length included in the data element are embedded with numerals in a binary form and the data is embedded with a character string in a text form and or numeral in the binary form.

The DICOM file generated by the modality 11 is recorded to a movable recording medium such as a flexible disk (FD), a compact disc-read only memory (CD-ROM), an a magneto optical (MO) disk, a digital versatile disc (DVD), a magnetic disk, or a semiconductor memory. The server 12 may obtain the DICOM file via the recording medium. In this case, the modality 11 is not necessarily connected to the server 12 via the network NI in the organization.

FIG. 3 is a block diagram showing the hardware structure of the server 12.

Referring to FIG. 3, the server 12 basically has a computer and, for example, comprises hardware including a central processing unit (CPU) 21, a memory 22, a hard disc (HD) 24 and a communication control device 25. The CPU 21 is mutually connected to components of the hardware forming the server 12 via a bus B1 as a common-signal transfer line. It is noted that the server 12 may have a drive 28.

The CPU 21 is a control unit that entirely controls the server 12, and loads, to the memory 22, a program stored in the HD 24, a program that is transferred from the network NI in the organization (shown in FIG. 1), is received by the communication control device 25, and is installed to the HD 24, or a program that is read from a recording medium 28 attached to the drive 28 and is installed to the HD 24 and executes the programs.

The memory 22 is a storage device having functions of a read only memory (ROM), a random access memory (RAM), and the like, stores an initial program loading (IPL), a basic input/output system (BIOS), and data, and is used as a work memory of the CPU 21 or as temporary storage of the DICOM file.

The HD 24 has a nonvolatile semiconductor memory. The HD 24 is a storage device that stores, as a DICOM file data base (DICOM file DB) 241, a program (application program, further including an OS) installed to the server 12 and the DICOM file. Further, the HD 24 can store the original image generated by the modality 11 or a thumbnail image. It is noted that a part or all of the information stored to the HD 24 is a DB and the DB is managed in a data base management system (DBMS) form. However, the present invention is not limited to this case and the information stored to the HD 24 may be managed in a file system form.

The communication control device 25 is, e.g., a communication interface (I/F) comprising an institute of electrical and electronics engineers (IEEE) 1394 port, a universal serial bus (USB) port, or an network interface card (NIC) for a local area network (LAN) connection, and controls communication in accordance with the standards. Further, the communication control device 25 has a function for connection to the network NI in the organization (shown in FIG. 1) via a phone line such as an analog modem, a terminal adapter (TA), a digital service unit (DSU), or an asymmetric digital subscriber line (ADSL) modem. With this function of the communication control device 25, the server 12 can be connected from the communication control device 25 to the network NI in the organization.

The recording medium 28*a* is detachable to the drive 28, the drive 28 reads data (including the program) recorded to the recording medium 28*a*, outputs the read data on the bus B1, and writes the data supplied via the bus B1 to the recording medium 28*a*.

FIG. 4 is a block diagram showing the hardware structure of the client viewer 13.

Referring to FIG. 4, the client viewer 13 basically has a computer, and further comprises basic hardware including a CPU 31, a memory 32, an HD 34, a communication control device 35, an input device 36, and a display device 37. The CPU 31 is mutually connected to the components of the hardware forming the client viewer 13 via a bus B2 as a common signal transfer line. The client viewer 13 may comprise a drive 38.

The CPU 31 executes the program stored in the memory 32 in response to an instruction by input with operation of the input device 36 by a user (interpreter such as a doctor). Alternatively, the CPU 31 loads, to the memory 32, the program stored in the HD 34, a program that is transferred from the network NI in the organization (shown in FIG. 1), is received from the communication control device 36, and is installed to the HD 34 or a program that is read from a recording medium 38*a* that is attached to the drive 38 and is installed to the HD 34, and executes the loaded program.

The memory 32 is a storage device having functions of a common component of the ROM and the RAM, stores the IPL, the BIOS, and the data, and is used for a work memory of the CPU 21 and temporary storage of the DICOM file.

The HD 34 has a nonvolatile semiconductor memory. The HD 34 is a storage device that stores a program (including not only an application program but also an OS) installed to the client viewer 13 and information on display-format DB 341 having information on the display-format as a database. The application program stored in the HD 34 includes a medical image display program 342. A description is given of the case of setting, as a DB, the information on the display-format stored in the HD 34 and of managing the DB in a DBMS form. However, the present invention is not limited to the case and, for example, the information on the display-format may be managed in a file system form. Alternatively, the OS may provide a graphical user interface (GUI) that performs basic operation with the input device 36 by frequently using graphics for displaying the information on the user.

The communication control device 35 is a communication I/F, and controls communication in accordance with the standards. Further, the communication control device 35 has a function for connection to the network NI in the organization (shown in FIG. 1) via a phone line. Thereby, the client viewer 13 can be connected from the communication control device 35 to the network NI in the organization.

As the input device 36, there is a keyboard or a mouse operable by a user, and an input signal in accordance with the operation is sent to the CPU 31. The input device 36 sends a request for displaying the medical image to the CPU 31. For example, the user selects a single patient with the input device 36 and the input device 36 thus sends a request to display the medical image of the single patient to the CPU 31.

As the display device 37, there is a monitor or the like. The display device 37 displays a setting image-plane of the information on the display-format, which will be described later, information of authentication, information of image request, and medical-image display information that executes and generates the medical image display program 342.

A recording medium 38a is detachable to the drive 38, and data recorded to the recording medium 38a is read and is output to a bus B2. Further, the drive 38 writes the data supplied via the bus B2 to the recording medium 38a. Herein, the medical image display program 342 executed by the CPU 31 can temporarily or infinitely be stored (recorded) to the recording medium 38a. The recording medium 38a can be provided as so-called package software.

Figure 5:
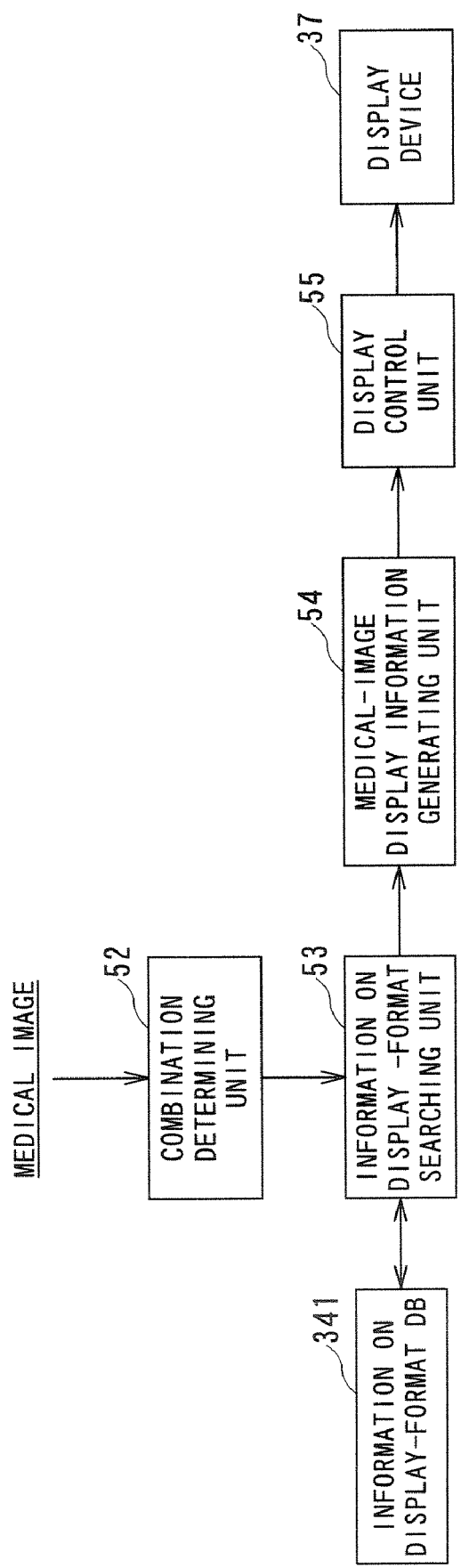
FIG. 5 is a functional block diagram.

FIG. 5 is a functional block diagram showing the medical image display system 10 obtained by executing the medical image display program 342 stored to the HD 34.

The CPU 31 (shown in FIG. 4) reads and executes the medical image display program 342 and the client viewer 13 thus functions as a combination determining unit 52, an information on display-format searching unit 53, a medical-image display information generating unit 54, and a display control unit 55.

When a plurality of DICOM files are sent to the combination determining unit 52 from the server 12 in response to a request of a display from the input device 36, the combination determining unit 52 has a function for determining a combination of image attributes about the medical image requested the display, on the basis of the tag information added to each medical image in the DICOM file.

The information on display-format searching unit 53 has a function for searching and obtaining information on a display-format corresponding to the combination of the image attributes about the request from the information on display-format DB 341 by comparing the combination of the image attributes about the request with the combination of the image attributes stored in the information on display format DB 341 in the HD 34.

The medical-image display information generating unit 54 has a function for generating medical-image display information by arranging the medical image made the request in accordance with the information on the display-format obtained by the information on display-format searching unit 53.

The display control unit 55 has a function for making the display device 37 display the medical-image display information generated by the medical-image display information generating unit 54 on (shown in FIG. 4).

The WS 18 shown in FIG. 1 may have an input device and a display device so as to have the same function as that of the client viewer 13, thereby commonly using the WS 18 corresponding to an image processing terminal, as an image display terminal.

Figure 6:
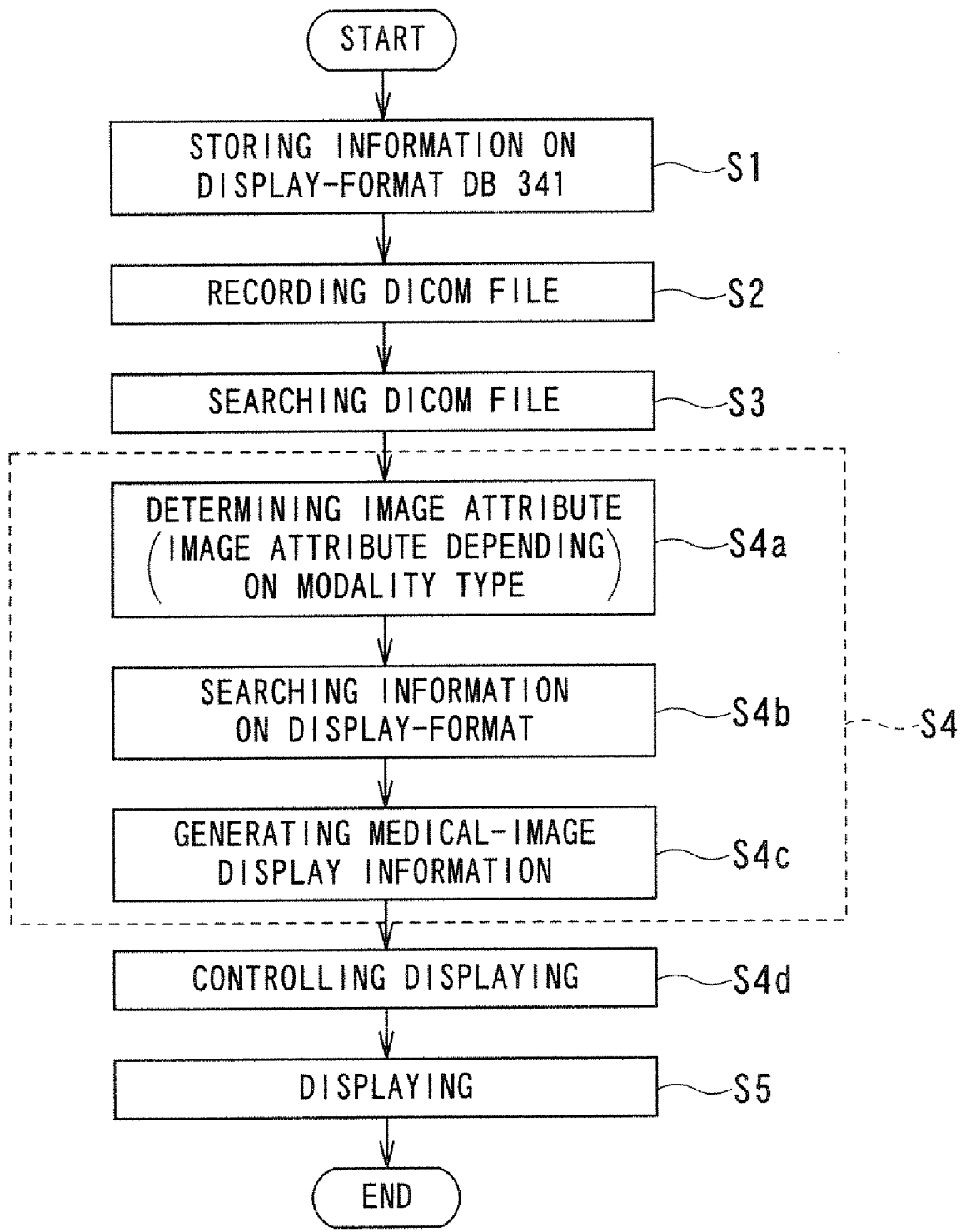
FIG. 6 is a flowchart according to the first embodiment of the present invention.

Subsequently, a description is given of a medical image display method, mainly with the medical image display system 10 shown in FIG. 1 and a flowchart shown in FIG. 6 according to the present invention. It is noted that a description is given of a medical image display method with a multi-modality, as the modality 11, obtained by combining the CT apparatus 11a, the MR apparatus 11b, and the CR apparatus 11c. However, the present invention is not limited to this.

First, prior to the interpretation of the user, the combination of a plurality of image attributes and the information on the display-format for each combination of the image attributes are set. For example, the image attribute is set as the image attribute depending on the modality type. The combination of the image attributes of the type of a plurality of the modalities 11 is allowed to have a correspondence to the information on the display-format, and the resultant data is stored as the information on display-format DB 341 to the HD 34 (shown in FIG. 4) of the client viewer 13 (in step S1).

FIG. 7 is a diagram showing the information on display-format DB 341 as a table.

Referring to FIG. 7, the information on display-format DB 341 is a table having the information on the display-format (first to third rows from the top) of a single image attribute and the information on the display-format (fourth to seventh rows from the top) as a combination of a plurality of the image attributes.

For example, the information on the display-format (sixth row from the top) having the combination of the image attributes of the CT apparatus, the MR apparatus, and the CR apparatus includes the information on the display frame of a CT image corresponding to the CT apparatus, the information on the display frame of an MR image corresponding to the MR apparatus, and the information on the display frame of a CR image corresponding to the CR apparatus. The information on the display frame of the CT image is set at the position on the display frame of a segment "(1 (lateral), 1 (longitudinal))" in the case of individually dividing an image-plane for medical image into two parts in the vertical direction and in the horizontal direction. The information on the display frame of the MR image is set at the position of a segment "(1, 1)" in the case of individually dividing the image-plane into two parts in the vertical direction and in the horizontal direction. Further, the information on the display frame of the CR image is set at the position of the display frame of a segment "(2, 1)-(2, 2)" in the case of individually dividing the image-plane in the vertical direction and horizontal direction. Although the position of the display frame is expressed as the position of a segment on the image-plane, the present invention is not limited to this. For example, the position on the display frame may be expressed as coordinates (pixel) on the image-plane.

Alternatively, if the combination of the image attributes includes the CT apparatus, the MR apparatus, and the CR apparatus (seventh row from the top), the information on the display frame of the CT image can be set at the position of the display frame of a segment "(1, 1)-(2, 1)", the information on the display frame of the MR image can be set at the position of the display frame of a segment "(1, 2)-(2, 2)", and the information on the display frame of the CR image can be set as "non-display".

Alternatively, a plurality of pieces of the information on the display-format may be set to a single image-attribute.

Herein, each image attribute has the information on the display frame. However, even if the image attributes are different, when each image attribute has the same examination, modality types are set as a single image attribute. In the case of the multi-modality, there is a compatibility between a plurality of modalities and a limitation based on the compatibility can be set. If one examination mixedly includes an RF image and an XA image, the RF image and the XA image are to be displayed at the same position of the display frame. On the other hand, even in the case of a series of examinations, the examinations are not set as a single one and the XA image can be displayed at the position of the display frame, different from that of the RF image.

Further, the contents of the display frame of the image attribute can be realized on the basis of the tag information of the DICOM file. The contents of the display frame are at least one of window width/window level (WW/WL) information, image quality information (information on gamma), rotation information, information on an enlargement factor, pan information, matrix size information, and information on stack display/tile display when a plurality of medical images correspond to a single image-attribute. Referring to FIG. 7, the contents of the display frame include only the information on the stack display/tile display. It is noted that the information on the stack display/tile display may include turn information on the unit basis of series in the case of the tile display. Further, when the information on the stack display/tile display is displayed as a tile, the information on the display frame may include information on the tile arrangement (e.g., tile arrangement 3×3).

Further, the contents of the display frame may information on a relative relationship, order information, cooperation information, and information on a relating portion.

The information on the relative relationship is information on a relative relationship between a matrix size of a first medical image corresponding to a first image attribute and a matrix size of a second medical image corresponding to a second image attribute when the different image attributes have different matrix sizes. For example, when the CT image and the CR image are arranged and displayed as the medical-image display information and the CT image is displayed with a matrix size of 100%, the contents of the display frame have a matrix size of 100% as the information on the relative relationship. Further, when the CT image is viewed with a matrix size of 100% at the timing of the user setting and the CR image is however viewed with a matrix size of 30%, the contents of the display frame of the CT image include the matrix size of 100% as the information on the relative relationship and the contents of the display frame of the CR image include the matrix size of 30%. In this case, the whole image of the CR image cannot be viewed depending on a window size or size of a display area. Further, when the matrix sizes are different in the combination of the image attributes, it is possible to set, as the contents of the display frame, information on the relative relationship between a matrix size of a first medical image corresponding to a first combination of the image attributes and a matrix size of a second medical image corresponding to a second combination of the image attributes. Further, the contents of the display frame can include a relationally-positional relationship to the pan information.

The order information is information on a sorting method of DESC or ASC of a plurality of medical images or a sorting method of the medical images in a series, when a plurality of medical images correspond to a single image attribute. The order information can be expressed by a series-number, ascending of series unique identifier (UID), or an ascending of the image number. It is noted that the sorting method of the images in the series can be changed depending on the modality, the image captured portion, and the apparatus.

The cooperation information is information as which medical image is cooperated and displayed among a plurality of medical images when a plurality of medical images correspond to a single image attribute. Depending on the cooperation information, a (one number)-th medical image is cooperated and displayed with an (another number)-th medical image on an examination or series among a plurality of medical images. Alternatively, depending on the cooperation information, positional information of the photographing system of the modality 11, e.g., the medical image having the same positional information on a bed is cooperated and displayed among a plurality of medical images. Alternatively, when there are medical images having different slice intervals, the medical images having the same slice width are cooperated and displayed by using the cooperation information. For example, when there are medical images having slice intervals of 1 mm and 2 mm, one medical image on a series of 2 mm is wound each time for winding two medical images having a series of 1 mm.

The information on the relating portion is information indicating whether or not a range of an image captured portion of a first medical image corresponding to a first image attribute is mainly displayed as a second medical image corresponding to a second image attribute, upon displaying the first medical image. For example, when the CR image is displayed within the range of the image captured portion, the information on the relating portion is information indicating whether or not a range of the image captured portion of the CR image is mainly displayed as the CT image.

Figure 8:
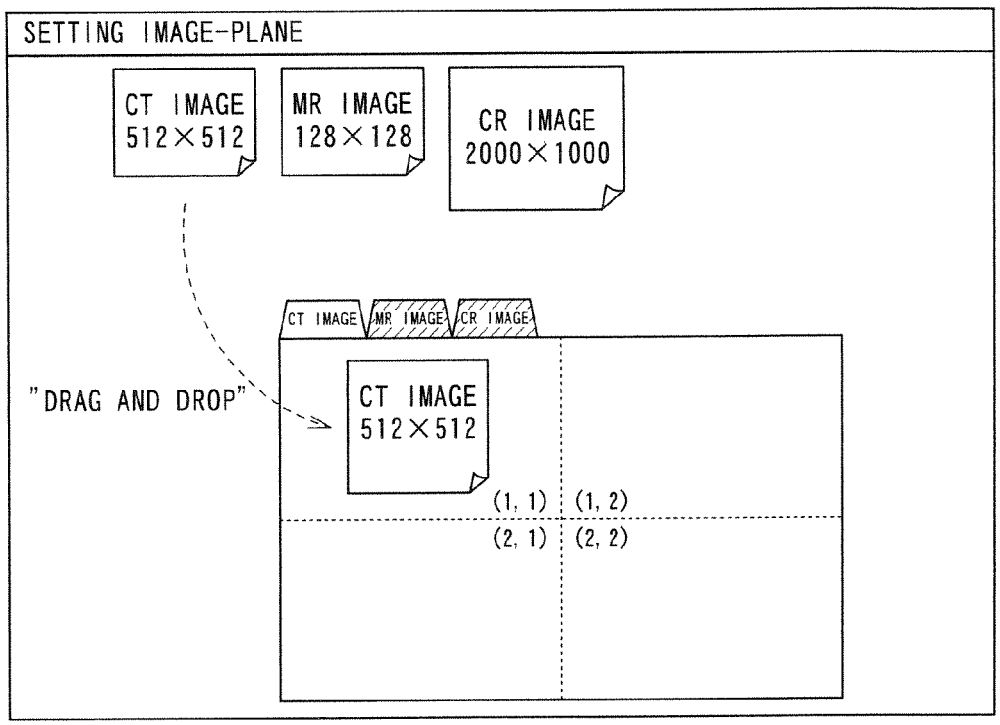
FIG. 8 is an initial state of a setting image-plane of information on a display-format.
Figure 9:
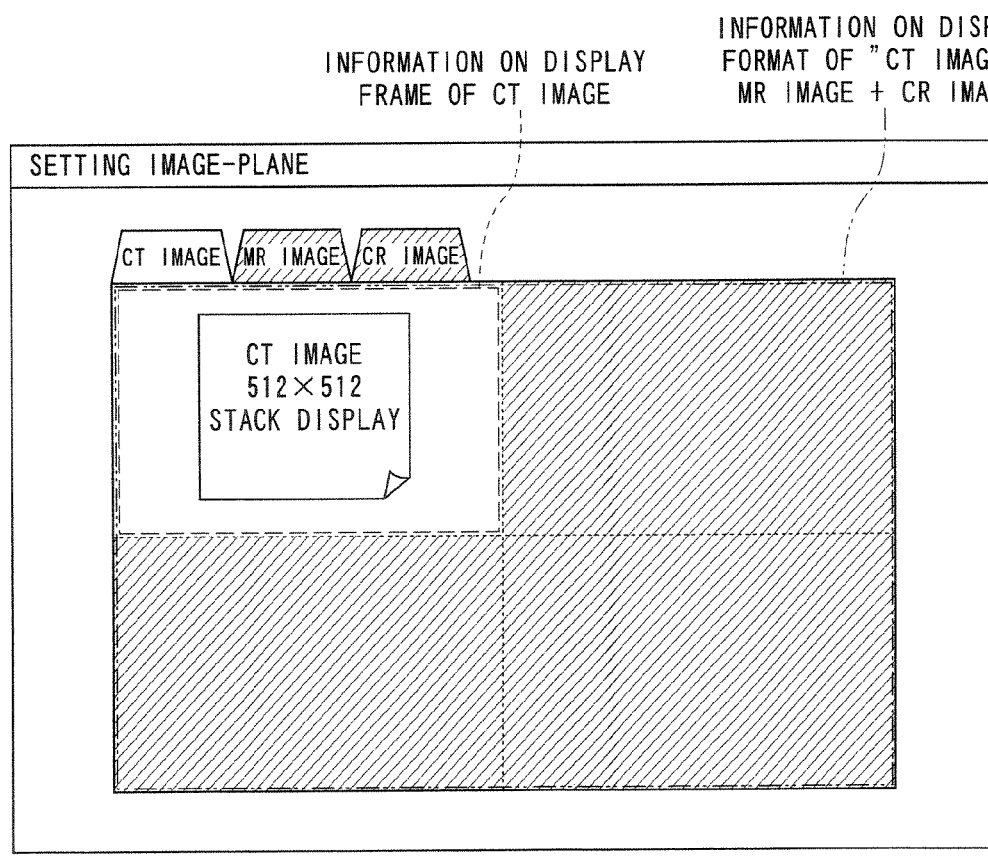
FIG. 9 is a setting-end state of a setting image-plane of information on a display-format.
Figure 10:
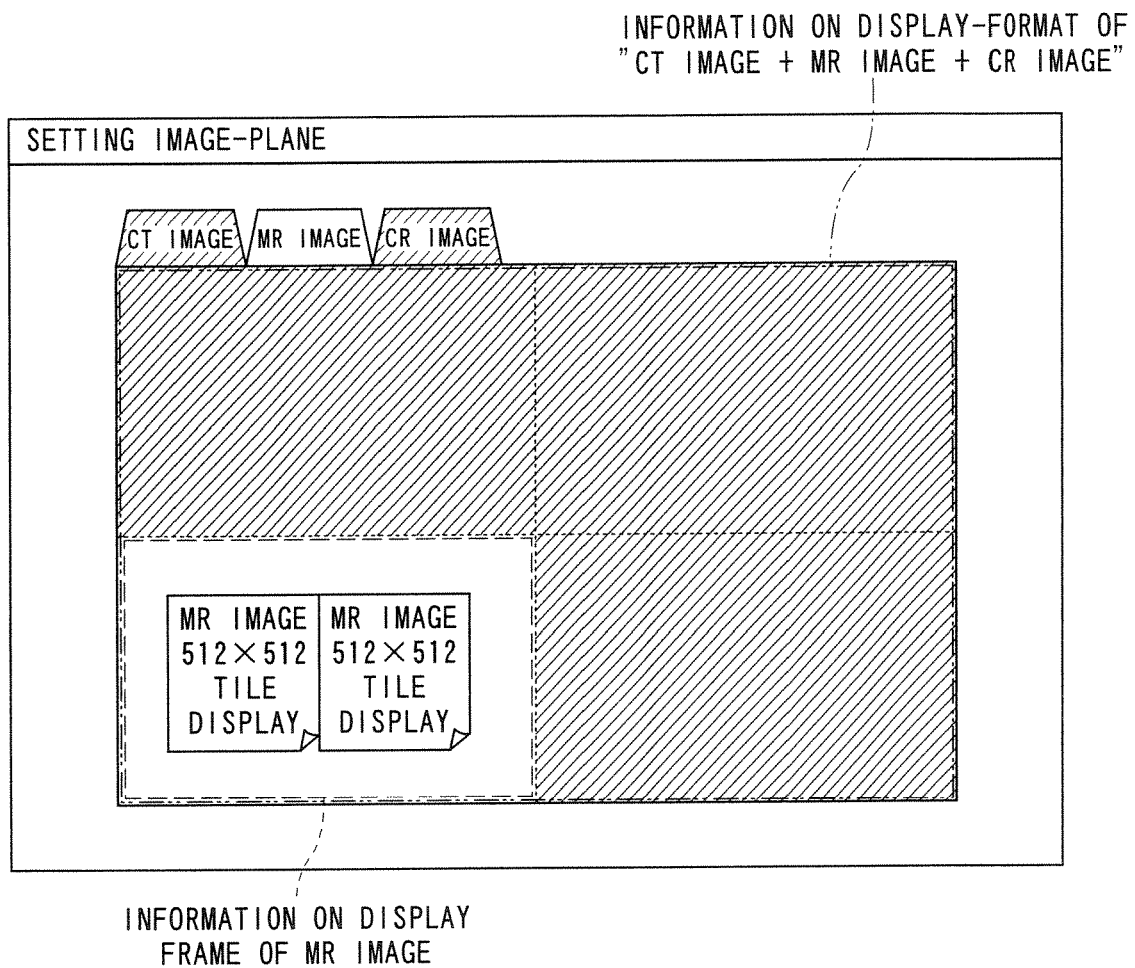
FIG. 10 is a setting-end state of a setting image-plane of information on a display-format.
Figure 11:
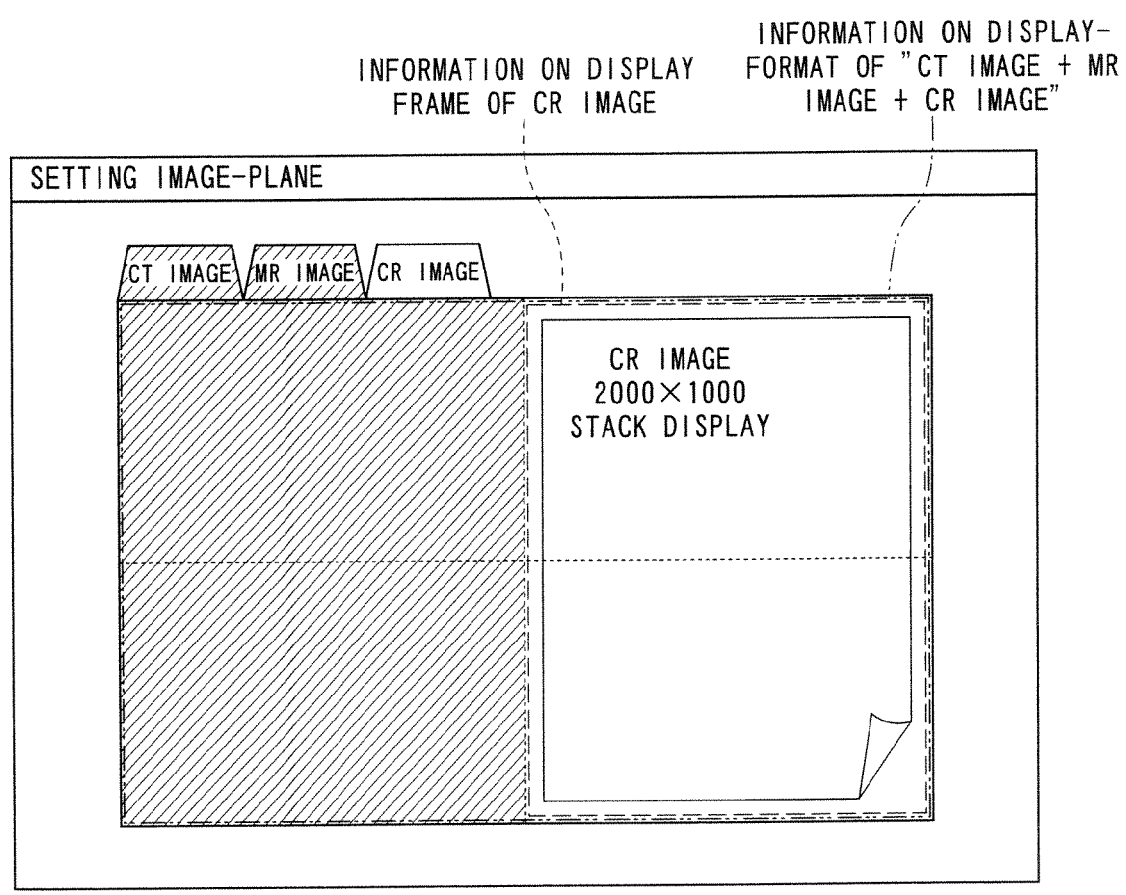
FIG. 11 is a setting-end state of a setting image-plane of information on a display-format.

FIGS. 8 to 11 are diagrams showing examples of a setting image-plane for setting the information on the display-format. FIG. 8 shows an initial state of the setting image-plane of the information on the display-format. FIGS. 9 to 11 show setting-end states of the setting image-plane of the information on the display-format.

As shown in FIGS. 8 to 11, the setting image-planes are GUI setting image-planes of the information on the display-format of the CT image, the MR image, and CR image when the combination of the image attributes comprises the CT apparatus, the MR apparatus, and the CR apparatus.

The top of the initial state shown in FIG. 8 shows thumbnail images having a simulated CT image obtained by simulating (representing) a displayed CT image, a simulated MR image obtained by simulating a displayed MR image, and a simulated CR image obtained by simulating a displayed CR image. The bottom of the initial state shows tabs for switching and using a plurality of image-planes within one window.

On the bottom of the initial state shown in FIG. 8, a title "CT image" is clicked with the input device 36, and the simulated CT image on the top is dragged and dropped to the position of the segment "(1, 1)" on the bottom. Further, if necessary, the stack display or the tile display can be selected and the stack display is displayed here. As mentioned above, the information on the display frame of the CT image corresponding to the CT apparatus shown in FIG. 9 is set.

Further, although not shown in FIG. 8, similarly, the "MR image" as a tab title is clicked and the simulated MR image on the top is dragged and dropped to the position of a "(1, 2)" on the bottom. Further, the tile display is selected as the display of the MR image. As mentioned above, the information on the display frame of the MR image corresponding to the MR apparatus shown in FIG. 10 is set. Further, although not shown in FIG. 8, similarly, the "CR image" as the tab title is clicked and the simulated CR image on the top is dragged and dropped to the position of the segment "(2, 1)-(2, 2)" on the bottom. As mentioned above, the information on the display frame of the CR image corresponding to the CR apparatus shown in FIG. 11 is set.

Therefore, on the setting image-planes of the information on the display-format shown in FIGS. 8 to 11, the information on the display-format can be easily set when the combination of the types of modalities includes the CT apparatus, the MR apparatus, and the CR apparatus.

When the image attribute is set as the image attribute depending on the modality type, as shown FIGS. 8 to 11, the type of medical image corresponding to the different modality type such as the "CT image", "MR image", or "CR image" is displayed as the tab title. However when the image attribute is set as the image attribute depending on the apparatus information, different application entity (AE) titles or different matrix sizes are displayed as the tab title. Further, when the image attribute is set as the image attribute depending on the shooting time zone, different shooting time zones such as the "oldest", "previous", and "latest" are displayed as the tab titles. In addition, when the image attribute is set as the image attribute depending on the image captured portion, the image attribute depending on the medical-image direction, the image attribute depending on the image processing information of the medical image, or the image attribute depending on the combination of a plurality of modalities.

Figure 12:
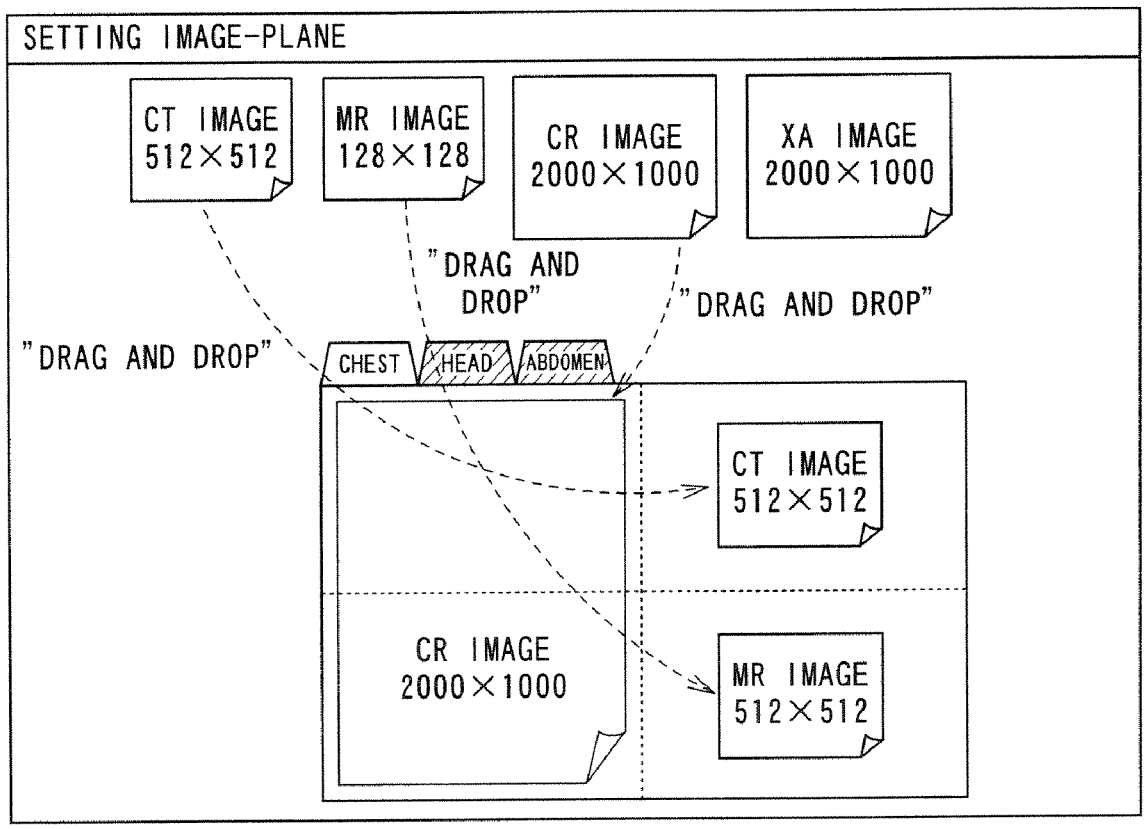
FIG. 12 is a setting image-plane of information on a display-format.

As other examples shown in FIGS. 8 to 11, the image attribute is set so as to distribute the image attributes depending on the image captured portion. In this case, the tab title is set as the "chest", "head" and "abdomen". As shown in a setting image-plane of the information on the display-format shown in FIG. 12, in a tab of the "chest", the CR image corresponding to the CR apparatus as the image attribute is dragged and dropped to the position of the left half of the image-plane, the CT image corresponding to the CT apparatus as the image attribute is dragged and dropped to the top of the right half, and the MR image corresponding to the MR apparatus as the image attribute is dragged and dropped to the position on the bottom of the right half, thereby setting the information on the display format of the image attributes or the information on the display frame of the chest.

In addition, although not shown, at the tab "head", the CT image is dragged and dropped to the left half and the MR image is dragged and dropped to the right half, thereby setting the information on the display frame of the image attribute or the information on the display format of the head. Further, although not shown, at the tab "abdomen", the MR image is dragged and dropped to the top of the left half, the CT image is dragged and dropped to the bottom of the left half, and the CR image is dragged and dropped to the right half, thereby setting the information on the display frame of the image attribute or the information on the display-format of the abdomen. On the image-plane that actually displays the image, the tab titles are used as a presetting function of the display position and as a changing function of display presetting of the client viewer 13. That is, the chest is selected with the changing function of the display presetting while viewing the client viewer 13. Thus, in accordance with the information on the display-format of the chest set by the tab "chest", the CR image is displayed to the left half of the image-plane, the CT image is displayed to the top of the right half, and the MR image is displayed to the bottom of the right half.

Subsequently, with the CT apparatus 11a, the MR apparatus 11b, and the CR apparatus 11c shown in FIG. 1, the image is captured and the individual DICOM file (shown in FIG. 2) is generated every image data from the image data for the medical image obtained by the image capturing operation. Under the control of a control device (not shown), the DICOM file is received to the server 12 via the LAN 15 and is recorded as the DICOM file DB 241 to the memory 22 of the server 12 (in step S2).

It is noted that the processing in steps S1 and S2 is repeated and the information on the display-format set in step S1 can thus be changed on the basis of the tag information in the DICOM file DB 241, stored in the server 12. For example, the DICOM file DB 241 of a patient is searched on the basis of the tag information in the DICOM file DB 241 stored in the server 12. It is assumed that the searched DICOM file includes, as the medical images of the patient, a plurality of the CT images, a plurality of the MR images, one CR image, and a plurality of digital radiography (DR) images. In this case, on the basis of the tag information of the DICOM files including the CT images, the MR images, the CR image, and the DR images, the top on the setting image-plane of the information on the display-format shown in FIG. 8 displays one simulated CT image obtained by simulating the CT images, one simulated MR image obtained by simulating the MR images, one simulated CR image obtained by simulating one CR image, and one simulated DR image obtained by simulating a plurality of the DR images.

The user operates the input device 36 forming the client viewer 13, thus determines a uniform resource locator (URL) for requesting the distribution of a DICOM file (requesting the display of the medical image) to the server 12, and accesses the server 12. Subsequently, a hypertext markup language (HTML) file is sent to the client viewer 13 from the server 12. With the input device 36, the user inputs a user ID and a password on the information of authentication, and sends them to the server 12. Thus, the server 12 determines whether the authentication is "YES" or "NO". After authenticating the user, the HTML file of the information of image requesting is sent to the client viewer 13. When the user is not authenticated, "NO" of the access to the server 12 is sent to the client viewer 13.

After the client viewer 13 receives the HTML file of the information of image requesting, the information of image requesting is displayed on the display device 37. Subsequently, the user inputs image specifying information for specifying the image, e.g., a patient ID, from the information of image requesting, the patient ID is thus sent to the server 12, and the display of the medical image is requested.

After receiving the patient ID, the server 12 searches the DICOM file of a desired patient on the basis of the patient ID from the DICOM file DB 241 stored in the HD 24 (in step S3). The searched and obtained DICOM file is sent to the client viewer 13 via the communication control device 25, the network NI in the organization, and the communication control device 35.

On the side of the client viewer 13, the CPU 31 executes the medical image display program 342 installed to the computer, thereby displaying the medical image sent from the server 12 on the display device 37 in accordance with the preset information on the display-format (in step S4). A specific sequence in step S4 is shown as follows.

First, the image attributes are determined on the basis of the tag information included in each DICOM file sent from the server 12. Subsequently, upon requesting the display of the medical image corresponding to a plurality of the image attributes, the combination of the image attributes requested the display is determined (in step S4a). In step S4a, by specifying the modality that generates the DICOM file from tag information of a tag (0008, 0060) at an incidental information area included in the DICOM file shown in FIG. 2, the combination of the image attributes of the modality type is determined. Herein, from the tag information of the tag (0008, 0060) at the incidental information area included in the DICOM file, it is determined that the combination of the image attributes of the modality type is the CT apparatus 11a, the MR apparatus 11b, and the CR apparatus 11c.

Subsequently, by combining the combination of the image attributes requested the display, determined in step S4a, with the combination of the image attributes stored in the information on display-format DB 341 in the HD 34, the information on the display-format corresponding to the combination of the image attributes requested the display is searched (in step S4b). Herein, from a table shown in FIG. 7, the information on the display-format is searched and obtained, when the combination of the image attributes of the modality type is the CT apparatus 11a, the MR apparatus 11b, and the CR apparatus 11c. Depending on the setting in step S1, a plurality of pieces of the information on the display-format can be obtained from a single combination of the image attributes can be obtained. In this case, the user can arbitrarily select the information on the display-format.

Subsequently, the image information requested the display is arranged in accordance with the information on the display-format obtained in step S4b, thereby generating the medical-image display information (in step S4c). Herein, when there is not the medical image corresponding to the image attribute, the position of the display frame in which the medical image corresponding to the image attribute is to be displayed is displayed as a default.

Subsequently, the medical-image display information generated in step S4c is displayed on the display device 37 (in step S4d).

As mentioned above, the display device 37 displays the medical-image display information (in step S5).

Even if the patients are different, it is possible to display the medical image on the same image-plane on the unit basis of the user or the client viewer 13 when the types of the modalities that capture the medical images of the patients are identical.

If the image attribute is set based on the apparatus information, e.g., as the image attribute of an AE title, the image attribute of facility information, the image attribute of the station name, or the image attribute of the matrix size, the medical image is displayed in accordance with the information on the display frame for each apparatus information based on the apparatus information included in the incidental information area of the DICOM file shown in FIG. 2.

In addition, if the image attribute is set as one of the image capturing time-interval, the medical image is arranged and displayed in accordance with the information on the display frame for each image capturing time-interval based on the image capturing time information included in the incidental information area in the DICOM file shown in FIG. 2. In order to assign the image capturing time to the image capturing time-interval, the image capturing time-interval needs to be set. By changing the position of the display frame depending on the image capturing time-interval, it is possible to relatively compare the latest medical image and the latest medical image with the oldest medical image and the medical image at a previous time zone of some degree, respectively.

Further, if the image attribute is one of the image captured portion, the medical image is arranged and displayed in accordance with the information on the display frame for each image captured portion based on information on the image captured portion (head, abdomen, and lower limbs) included in the incidental information area included in the DICOM file shown in FIG. 2.

Further, if the image attribute is one of the medical image direction, the medical image is arranged and displayed in accordance with the information on the display frame of each medical image direction based on information on the axial, sagittal, or coronal cross-sectional direction included in the incidental information area of the DICOM file shown in FIG. 2.

In addition, if the image attribute is one of the information on the image processing, the medical image is arranged and displayed in accordance with the information on the display frame for each information on the image processing based on information on the image processing such as SVR processing, MaxIP processing, MinIP processing, IP processing, and MPR processing, included as the tag information (private tag information, etc.) in the incidental information area of the DICOM file shown in FIG. 2 and information such as, a volume rendering (VR), T1 (vertical releasing time), T2 (horizontal releasing time), YES/NO of contrast agent, and fusion.

In addition, if the image attribute is one of the server 12, the medical image is arranged and displayed in accordance with the information on the display frame for each server 12 based on server information included as the tag information (private tag information, etc.) included in the incidental information of the DICOM file shown in FIG. 2. The medical image is collected from the server 12, and a typical image is displayed in accordance with the information on the display frame for each typical image of the server 12. In general, the medical images of different patients cannot be displayed on the same image-plane. However, if the image attribute is one of the server 12, the medical images of different patients can be specially displayed on the same image-plane. The information is stored to the information on the display frame by unchecking the patient ID or displaying a mark indicating sample data (for case comparison). As a specific using case, when the user registers the medical image of a preferable case to the medical image display system 10, the medical image display system 10 presets the case so as to allow the user to always select the case, and displays the case if the user views the medical image, needs it, and calls it. Further, when the user adjusts the position of the display frame and when he/she requires the display of the sample data, the sample data is stored to be displayed as the information on the display frame.

Accoding to the medical image display system 10, the medical image display method, and the medical image display program 342, various medical images generated by the multi-modality can be easily arranged to the proper positions. Thus, it is possible to suppress the troublesomeness of operation for arranging the medical images generated upon operating the client viewer 13 by the user and to support efficiency of comparison and interpretation of various medical images, executed on the client viewer 13.

Figure 13:
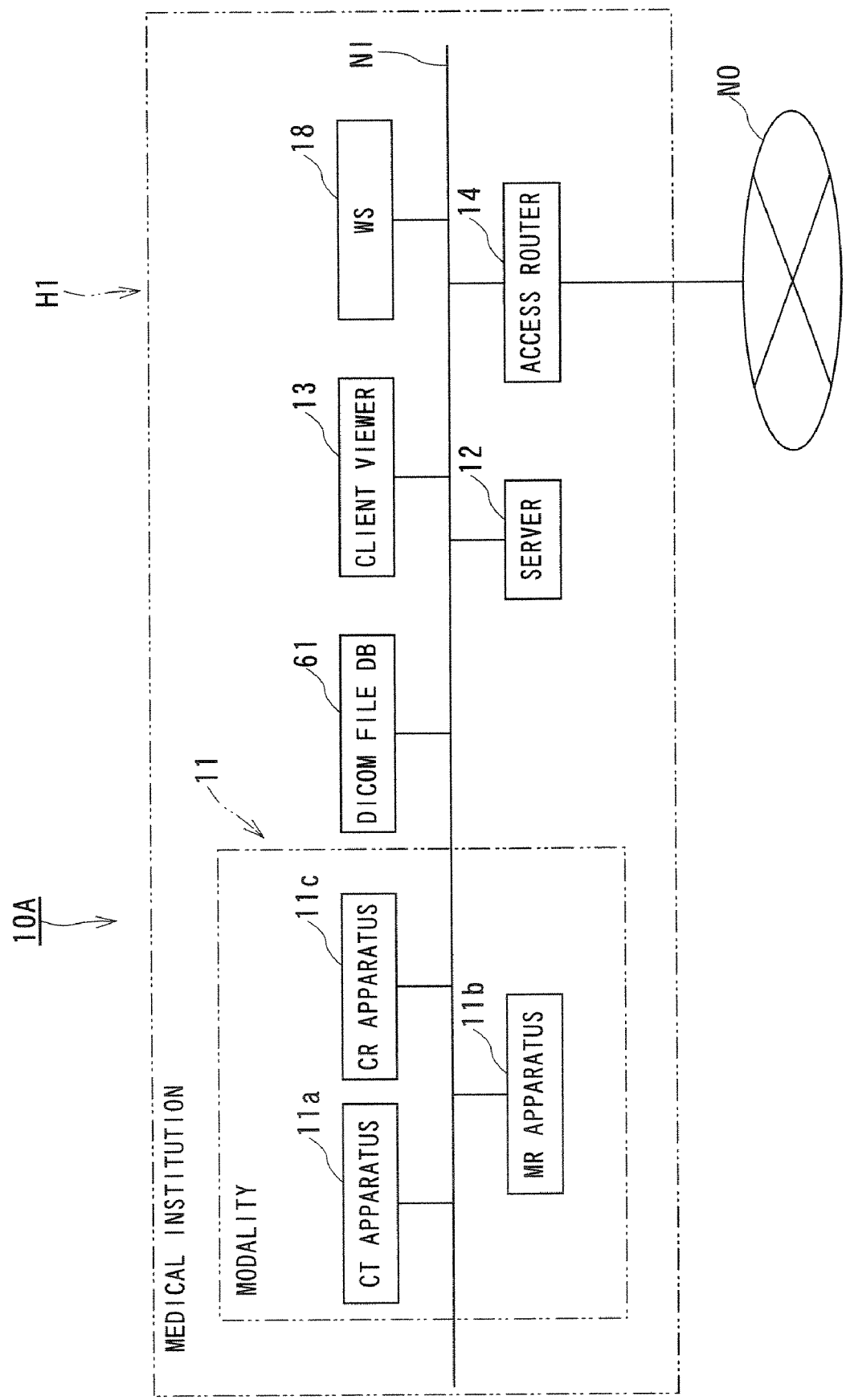
FIG. 13 is a schematic diagram showing the entire outline of the medical image display system according to the second embodiment of the present invention.

FIG. 13 is a schematic diagram showing a medical image display system according to the second embodiment of the present invention.

Referring to FIG. 13, a medical image display system 10A is shown. The medical image display system 10A has a DICOM file DB 61 as the DICOM file storage device on the network NI in the organization. A part or all of information stored in the DICOM file storage device is managed as a DB in a DBMS form. However, the present invention is not limited to this and the information may be managed in a file system form.

The DICOM file DB 61 is a network attached storage (NAS) that stores the image data of the medical image generated by the modality 11, and stores an original image generated by the modality 11 and a DICOM image generated on the basis of the original image in accordance with the type of image. That is, the DICOM file DB 61 can realize information storing system.

In the medical image display system 10A shown in FIG. 13, the same components as those in the medical image display system 10 shown in FIG. 1 are designated by the same reference numerals. Further, the medical image display method with the medical image display system 10A has the same operations shown in the flowchart in FIG. 6. Consequently, a description thereof is omitted.

Accoding to the medical image display system 10A, the medical image display method, and the medical image display program 342, various medical images generated by the multi-modality are easily arranged at the proper positions. Accordingly, it is possible to suppress the troublesomeness of the operation for arranging the medical images generated when the user operates the client viewer 13 and to support the efficiency of comparison and interpretation of various medical images, executed on the client viewer 13.

What is claimed is:

1. A multi-modality medical image display system, comprising:
   a storage device configured to store a combination of different image attributes, each indicating an attribute of an image, in association with a display layout including respective display sizes of each image attribute of the image attributes, the display sizes of the display layout controlling how the images of the combination will be displayed on a same image plane;
   a client viewer having at least one of a first display frame and a second display frame;
   an input device configured to request a display of a plurality of medical images;
   a combination determining unit configured to determine, if the plurality of medical images have different image attributes, a determined combination of the different image attributes, based on incidental information that is assigned to the requested plurality of medical images;
   a searching unit configured to compare the determined combination with the stored combination and, based on the comparison, to search the storage device and obtain therefrom one of a plurality of display layouts stored in the storage device that corresponds with the determined combination;
   a medical-image display information generating unit configured to generate medical-image display information by arranging the requested plurality of medical images in accordance with the one of the plurality of display layouts obtained by the searching unit; and
   a display control unit configured to control display of the medical-image display information.

2. A multi-modality medical image display system according claim 1, wherein the input device makes the request on a single patient.

3. A multi-modality medical image display system according to claim 1, wherein the different image attributes are set as a plurality of image attributes depending on modality types.

4. A multi-modality medical image display system according to claim 3, wherein when each image attribute has the same examination, modality types are set as a single image attribute.

5. A multi-modality medical image display system according to claim 1, wherein the different image attributes are set as a plurality of image attributes depending on image capturing time-intervals.

6. A multi-modality medical image display system according to claim 1, wherein the different image attributes are set as a plurality of image attributes depending on image captured portions.

7. A multi-modality medical image display system according to claim 1, wherein the one of the plurality of display layouts includes information on a display frame for each of the different image attributes, the information on the display frame for each of the different image attributes includes a position of a display frame as information where the plurality of medical images is displayed on an image-plane, and the position of the display frame is expressed as a segment position on the image-plane.

8. A multi-modality medical image display system according to claim 1, wherein the different image attributes are set as a plurality of image attributes depending on information on image processing.

9. A multi-modality medical image display system according to claim 1, wherein the different image attributes are set as a plurality of image attributes depending on apparatus information.

10. A multi-modality medical image display system according to claim 9, wherein the apparatus information is an application entity title, facility information, a model name, a station name, or a matrix size.

11. A multi-modality medical image display system according to claim 1, wherein the different image attributes are set as a plurality of image attributes depending on medical image directions.

12. A multi-modality medical image display system according to claim 1, wherein the different image attributes are set as a plurality of image attributes depending on server types that store the image information.

13. A multi-modality medical image display system according to claim 1, wherein the one of the plurality of display layouts includes information on the display frame for each of the different image attributes, the information on the display frame for each of the different image attributes includes contents of the display frame indicating how the plurality of medical images are displayed.

14. A multi-modality medical image display system according to claim 13, wherein order information indicating a sorting manner of a plurality of pieces of image information is set as the contents of the display frame, when the pieces of the image information corresponds to a single image-attribute.

15. A multi-modality medical image display system according to claim 13, wherein cooperation information indicating which image information is cooperatively displayed among a plurality of pieces of image information is set as the contents of the display frame, when the pieces of the image information corresponds to a single image-attribute.

16. A multi-modality medical image display system according to claim 15, wherein the cooperation information enables the cooperative display of information of a first image and information of a second image on an examination or series, among the pieces of the image information.

17. A multi-modality medical image display system according to claim 15, wherein the cooperation information enables the cooperative display of the image information having the same positional information of a photographing system of a modality among the pieces of the image information.

18. A multi-modality medical image display system according to claim 15, wherein the cooperation information enables the cooperative display of the image information having the same slice width when a plurality of pieces of the image information on a series having different slice intervals exist as the pieces of the image information.

19. A multi-modality medical image display system according to claim 13, wherein the contents of the display frame are at least one of window width/window level information, image quality information, rotation information, information on an enlargement factor, pan information, matrix size information, and information on stack display/tile display when a plurality of pieces of image information corresponds to a single image-attribute.

20. A multi-modality medical image display system according to claim 13, wherein, when matrix sizes in the combination of the different image attributes are different, information on a relative relationship between the matrix size of the image information corresponding to a first image attribute and the matrix size of the image information corresponding to a second image attribute is set as the contents of the display frame.

21. A multi-modality medical image display system according to claim 13, wherein, when matrix sizes in the combination of the different image attributes are different, information on a relative relationship between the matrix size of the image information corresponding to a first combination of the image attributes and the matrix size of the image information corresponding to a second combination of the different image attributes is set as the contents of the display frame.

22. A multi-modality medical image display system according to claim 13, wherein, upon display of a first medical image corresponding to a first image attribute within a range of an image captured portion, information on a relating portion indicating whether or not a range of the image captured portion in the first medical image is mainly displayed as a second medical image corresponding to a second image attribute is set as the contents of the display frame.

23. A multi-modality medical image display system according to claim 1, wherein the one of the plurality of display layouts includes information on a display frame for each of the different image attributes, and the information on the display frame for each of the different image attributes includes information indicating whether or not the plurality of medical images is displayed.

24. A multi-modality medical image display system according to claim 1, wherein the plurality of display layouts are set for every user.

25. A multi-modality medical image display system according to claim 1, wherein the plurality of display layouts are set for each image display terminal.

26. A multi-modality medical image display system according to claim 1, wherein the plurality of display layouts are set for each system.

27. A multi-modality medical image display method, comprising:
storing in a storage device a combination of different image attributes, each indicating an attribute of an image, in association with a display layout including respective display sizes of each image attribute of the image attributes, the display sizes of the display layout controlling how the images of the combination will be displayed on a same image plane;
requesting a display of a plurality of medical images;
determining, if the plurality of medical images have different image attributes, a determined combination of image attributes based on incidental information that is assigned to the requested plurality of medical images;
comparing the determined combination with the stored combination and, based on the comparison, searching the storage device and obtaining therefrom one of a plurality of display layouts stored in the storage device that corresponds with the determined combination;
generating medical-image display information by arranging the requested plurality of medical images in accordance with the one of the plurality of display layouts obtained in the obtaining step; and
displaying the medical-image display information.

28. A non-transitory computer readable medium encoded with a computer readable medical image display program configured to cause an information processing apparatus to execute a method, the method comprising:
storing in a storage device a combination of different image attributes, each indicating an attribute of an image, in association with a display layout including respective display sizes of each image attribute of the image attributes, the display sizes of the display layout controlling how the images of the combination will be displayed on a same image plane;
requesting a display of a plurality of medical images;
determining, if the plurality of medical images have different image attributes, a determined combination of image attributes based on incidental information that is assigned to the requested plurality of medical images;
comparing the determined combination with the stored combination and, based on the comparison, searching the storage device and obtaining therefrom one of a plurality of display layouts stored in the storage device that corresponds with the determined combination;
generating medical-image display information by arranging the requested plurality of medical images in accordance with the one of the plurality of display layouts obtained in the obtaining step; and
displaying the medical-image display information.

* * * * *